United States Patent [19]
Gergely et al.

[11] Patent Number: 5,888,544
[45] Date of Patent: Mar. 30, 1999

[54] EFFERVESCENT SYSTEM FOR EFFERVESCENT TABLETS AND EFFERVESCENT GRANULES

[75] Inventors: Gerhard Gergely, Gartengasse 8; Irmgard Gergely; Thomas Gergely; Stefan Gergely, all of Vienna, Austria

[73] Assignee: Gerhard Gergely, Vienna, Austria

[21] Appl. No.: 867,446

[22] Filed: Jun. 2, 1997

[30] Foreign Application Priority Data

Jun. 20, 1996 [CH] Switzerland .............................. 1541/96

[51] Int. Cl.⁶ ...................................................... A61K 9/46
[52] U.S. Cl. ............................................ 424/466; 424/489
[58] Field of Search .................................. 424/466, 489, 424/490, 465

[56] References Cited

U.S. PATENT DOCUMENTS

3,105,792  10/1963  White ........................................ 167/57
3,984,527  10/1976  Gancy et al. ............................. 423/425

FOREIGN PATENT DOCUMENTS

A 55-7246  1/1980  Japan .
2-174004  10/1986  United Kingdom .

Primary Examiner—Thurman K. Page
Assistant Examiner—James M. Spear
Attorney, Agent, or Firm—Oliff & Berridge, PLC

[57] ABSTRACT

The effervescent system for effervescent tablets and/or effervescent granules contains, on the one hand, particles of a solid, edible, organic acid and, on the other hand, particles of at least one alkali metal bicarbonate, of which at least 1, preferably from 2 to 4, but at most 10, preferably at most 8, % by weight are superficially converted into dry alkali metal carbonate free of water of crystallization. The acid particles, preferably citric acid particles, can be covered in a manner known per se by partial reaction with at least one carbonate and/or bicarbonate, preferably from about 20 to 40% by weight thereof. The conversion mentioned is carried out by a procedure in which commercial alkali metal bicarbonate particles are heated in a vacuum vessel at less than 40, preferably less than 20, in particular less than 10, mbar at above 60° C., preferably between 80° C. and 120° C., in particular at about 100° C., and are cooled to below 60° C., preferably to below 50° C., after a time predetermined by the desired layer thickness, while maintaining the vacuum. The alkali metal carbonate particles evolve only a little $CO_2$ even on storage at elevated temperature, and the formation of free salicylic acid (fSA) from any acetylsalicylic acid mixed with the effervescent system remains very small.

8 Claims, 4 Drawing Sheets fSA = 0,23%

- fSA = 0,16% —▲—
- fSA = 0,25% —◆—
- fSA = 0,18% —✕—

FIG.8      fSA = 0,81%

EFFERVESCENT SYSTEM FOR EFFERVESCENT TABLETS AND EFFERVESCENT GRANULES

BACKGROUND OF THE INVENTION

1. Field of the Invention

The invention relates to an effervescent system for effervescent tablets and effervescent granules according to the precharacterizing clause of claim 1, and a process for the preparation of the effervescent system according to the precharacterizing clause of claim 5. Such an effervescent system has been disclosed in U.S. Pat. No. 3,105,792, the content of which is hereby considered to have been disclosed for the purposes of the present description, and according to which alkali metal bicarbonate is heated for a short time to relatively high temperatures or for a longer time to lower temperatures, for example spread over large cups over which air flows.

2. Description of Related Art

It is known that, on the one hand, the stability of sodium bicarbonate to organic acids, for example citric acid or tartaric acid, is reduced by virtue of the fact that, without special measures, reactions occur between sodium bicarbonate and the acid owing to residual moisture which is always present. On the other hand, the sodium bicarbonate tends to undergo thermal decomposition by itself, even at only slightly elevated temperatures, according to the formula $$2NaHCO_3 = Na_2CO_3 + CO_2 + H_2O.$$

The reaction with the acid can be prevented—but only partially—by passivating it, i.e. causing it to undergo a partial reaction at the surface with a carbonate or bicarbonate. A further improvement in the stability results if the sodium bicarbonate particles themselves are partially converted at the surface to sodium carbonate, as described in U.S. Pat. No. 3,105,792. The resulting water is at least partially incorporated as water of crystallization in the sodium carbonate, which however is in turn reactive by its very nature.

However, a more exact investigation of the process described in U.S. Pat. No. 3,105,792 showed that it was possible to achieve an improvement compared with commercial alkali metal bicarbonate particles with regard to the stability of the effervescent system and any active ingredients, for example acetylsalicylic acid, using alkali metal bicarbonate particles which are coated with alkali metal carbonate. However, the degree of improvement was still unsatisfactory, particularly in the case of relatively long storage times and/or relatively high temperatures, as may readily occur in hot countries.

SUMMARY OF THE INVENTION

During research into the causes of this unsatisfactory behaviour, it was found that evidently the water liberated on heating the alkali metal bicarbonate could not be removed or at least could not be completely removed but is incorporated as water of crystallization in the alkali metal carbonate formed in the surface layer of the particles, which water of crystallization cannot be removed at the stated reaction temperatures and in the stated reaction times and subsequently leads to secondary reactions. Moreover, it is important that the resulting alkali metal carbonate is uniformly distributed over the surface of the alkali metal bicarbonate crystals, which evidently cannot be adequately achieved by heating on cups, even by turning over a few times.

The stability measurements were carried out from two different points of view, firstly by determining the $CO_2$ evolution under the action of heat and secondly by selecting a sensitive effervescent system, such as, for example, one containing acetylsalicylic acid, and the amount of free salicylic acid formed from acetylsalicylic acid under the influence of heat and of the residual moisture was determined by means of HPLC. In fact, the acetylsalicylic acid itself also reacts with the sodium bicarbonate, with the result that unstable systems appear relatively rapidly. The $CO_2$ evolution under the action of heat is measured as follows: In a gas-tight measuring setup, the evolution of $CO_2$ from an effervescent system under thermal stress is measured adiabatically. This provides information about the stability of the formulation on prolonged storage at room temperature. The determination is a measure of both any residual water present in the effervescent base and the course of the degradation reaction of the active ingredient (e.g. acetylsalicylic acid), in which water is formed, which subsequently liberates $CO_2$ again.

The sample (about 200 g of tablets or effervescent granules) is thermostated in a tightly sealed brass bomb in a water bath for 20 minutes at 45° C. After this time, the bomb is connected to the measuring setup. This consists of a U-tube which is filled with silicone oil and sealed gas-tight by means of a solenoid valve. As a result of the $CO_2$ gas formed, the meniscus of the sealing liquid changes. As soon as this meniscus is forced below a preselected level, a light barrier switches the valve and the measurement process begins again (=1 pulse; the measured gas volumes per pulse are between 10 and 50 μl, depending on the selected setting). The switching pulses of the valve are recorded.

The total number of pulses over the measuring time corresponds to the total amount of $CO_2$ formed, and the distance between the pulses or the pulses per time interval (e.g. 10 min) provides information about the behaviour of the system; the function $n = f(\Delta t)$ converges towards 0 in the case of a stable product.

It was found that, from an effervescent tablet containing acetylsalicylic acid and untreated sodium bicarbonate, from 5 to 10% by weight of the acetylsalicylic acid had been converted into free salicylic acid after only a few hours at 45° C.; with sodium bicarbonate modified according to the U.S. Pat. No. stated at the outset, however, the relevant figure was still more than 1, in general about 5, % by weight.

It is therefore the object of the invention to provide an effervescent system according to the characterizing clause of claim 1, which has a stability, with regard to $CO_2$ evolution and acetylsalicylic acid degradation, which if possible is an order of magnitude better than that of the known effervescent system. Such a system is now proposed according to the invention for the first time through the absence of water of crystallization in the alkali metal carbonate layer. The preparation was possible for the first time in a surprising manner by application of a vacuum, as described in the characterizing clause of claim 5, in particular by means of particularly powerful pumps which transform the water of reaction formed during the heat treatment or from the conversion of the alkali metal bicarbonate into the alkali metal carbonate immediately into the vapour state and remove said vapour before it can be incorporated as water of crystallization into the alkali metal carbonate layer formed. Alkali metal bicarbonate particles treated in this manner also have an essentially cohesive carbonate layer and, under the abovementioned measurement conditions, give only less than 0.5, in general from about 0.1 to 0.2, % by weight of free salicylic acid.

Advantageous further embodiments of the invention are described in the characterizing clauses of the dependent Claims.

DESCRIPTION OF THE DRAWINGS

FIG. 8 shows the $CO_2$ evolution of an effervescent system with medium-coarse sodium bicarbonate having 6% conversion without a vacuum.

DETAILED DESCRIPTION OF THE PREFERRED EMBODIMENTS

Figure 1:
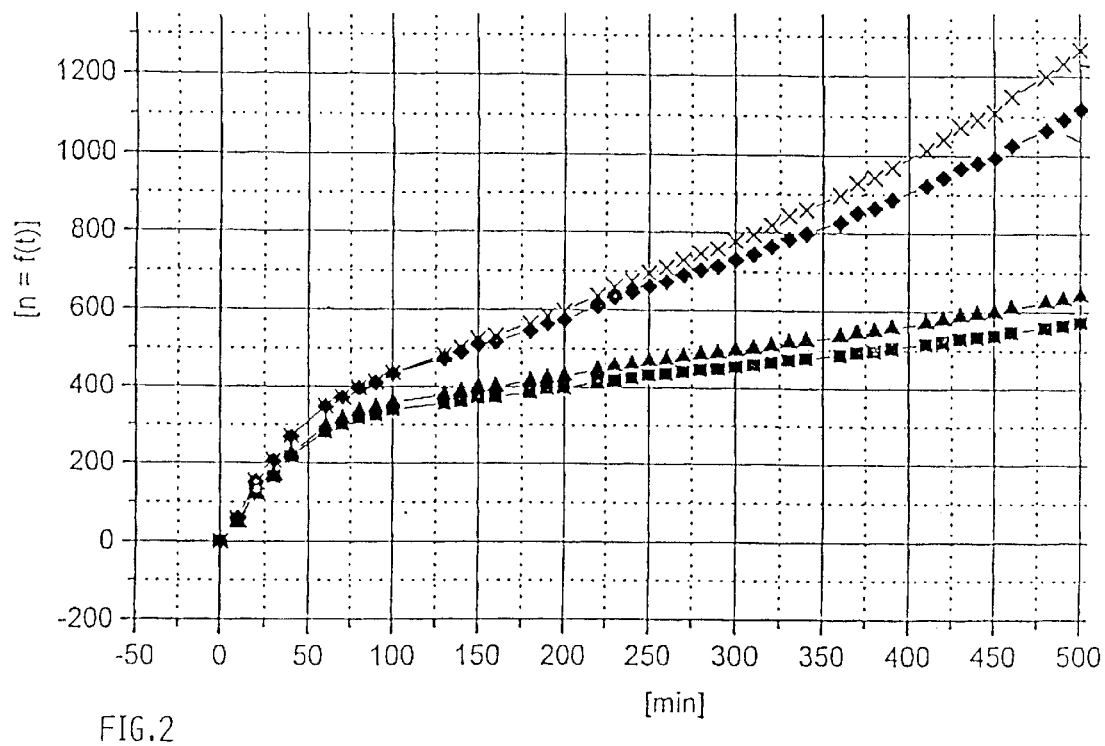
FIG. 1 shows the $CO_2$ evolution of two parallel experiments. In one experiment, the air is cooled and in the other experiment, the pressure is reduced.

Since thermal convection is extremely poor under a high vacuum, it is advisable to mount the jacket heating with relatively high temperatures of from about 100° C. to about 120° C. The sodium bicarbonate begins to be transformed into sodium carbonate at its surface between 80° and 100° C., it being possible occasionally for abrupt thermal decompositions to occur and for the $CO_2$ being evolved and the steam to cause the vacuum to increase by about 20 to 30 mbar, even with a powerful pump.

It is very particularly important for the process that the jacket is immediately cooled on reaching the desired degree of conversion and the resulting mixed crystals are also cooled under a high vacuum so that termination of the process should never take place at a product temperature of above 60° C., preferably never at a product temperature above 50° C. Only thereafter should the material be removed from the vacuum vessel.

The conversion state can also very readily be established under the microscope in reflected or transmitted light since the resulting crystals have become uniformly opaque in reflected light and nontransparent in transmitted light.

If such sodium bicarbonates are used in effervescent tablet formulations containing, for example, aspirin, it is possible, under certain circumstances, to obtain stable tablets even with untreated citric acid—without particular passivation measures.

A further advantage of this type of converted sodium bicarbonate is that strong electrical binding forces are generated in the crystal structures by the lattice defects, with the result that hard tablets can be obtained on compression.

The effect according to the invention can in theory be explained as follows: the process for the partial conversion of sodium bicarbonate into sodium carbonate without a vacuum according to U.S. Pat. No. 3,105,792 is actually not substantially different from the addition of sodium carbonate.

If however, according to the invention, the outer layer on the alkali metal bicarbonate crystals is converted into anhydrous sodium carbonate, the $H_2O$ and $CO_2$ formed in the interior in the thermal reaction of the sodium bicarbonate during storage of the tablet is immediately converted back into sodium bicarbonate by the adjacent layer of sodium carbonate. However, dry bicarbonate is far less susceptible to thermal decomposition than bicarbonate in the presence of even only traces of moisture.

This process may oscillate back and forth and stabilizes the entire system. It is comparable with the precipitation of more slightly soluble sodium bicarbonate by the introduction of carbon dioxide gas into solutions of sodium carbonate, or with the formation of the sesquicarbonate (Trona, $NaHCO_3 \cdot Na_2CO_3 \cdot 2H_2O$), which is formed in nature as the stable form between sodium bicarbonate and sodium carbonate (with two molecules of water of crystallization) in the salt lakes. A similar process occurs in the oscillation between inner and outer layer of the alkali metal bicarbonate crystal, where Trona-like processes take place as the end product of the equilibrium of the reaction.

If, however, the sodium carbonate is not dry and/or already contains water of crystallization, this process cannot take place or can take place only partially since a sodium carbonate which already contains water of crystallization is no longer capable of this reaction. The requirement for the stability of such structures is therefore the complete absence of moisture and in particular of water of crystallization.

The invention is illustrated in more detail by way of example with reference to the drawing. FIG. 1 shows the $CO_2$ evolution of a product according to U.S. Pat. No. 3,105,792 as part of the prior art.

(EXAMPLE 1)

A granulation vessel having a jacket temperature of 110° C. is filled with 8 g of medium-coarse sodium bicarbonate (60–65% by weight between 0.1 and 0.2 mm) and heated for 3 hours while passing through air until the product temperature has exceeded 100° C. Thereafter, the material is cooled to 55° C. for 2 hours, one part (X and ♦) in the room air and another part (▲ and ■) in the vessel while passing through air at slightly reduced pressure. A conversion of 6% results.

In each case, 1000 parts by weight of sodium bicarbonate treated in this manner are compressed with 750 parts by weight of citric acid, 550 parts by weight of acetylsalicylic acid and 50 parts by weight of caffeine to give tablets weighing 2.3 g each, which are then subjected to the abovementioned test for determining the $CO_2$ evolution. The curves of the $CO_2$ evolution are shown in FIG. 1, in each case two parallel experiments with cooling in the room air (X and ♦) with 5.27% of free salicylic acid and in the vessel while passing through air at slightly reduced pressure (▲ and ■) with 1.88% of free salicylic acid, which nevertheless denotes an improvement, although a small one.

EXAMPLE 2

The process according to Example 1 is repeated, except that the granulation vessel is a vacuum vessel to which a pump having a nominal pumping capacity of 100 m³/h is connected. It is evacuated to 5 mbar; the vacuum is always kept below 20 mbar even during the treatment and the cooling.

Figure 2:
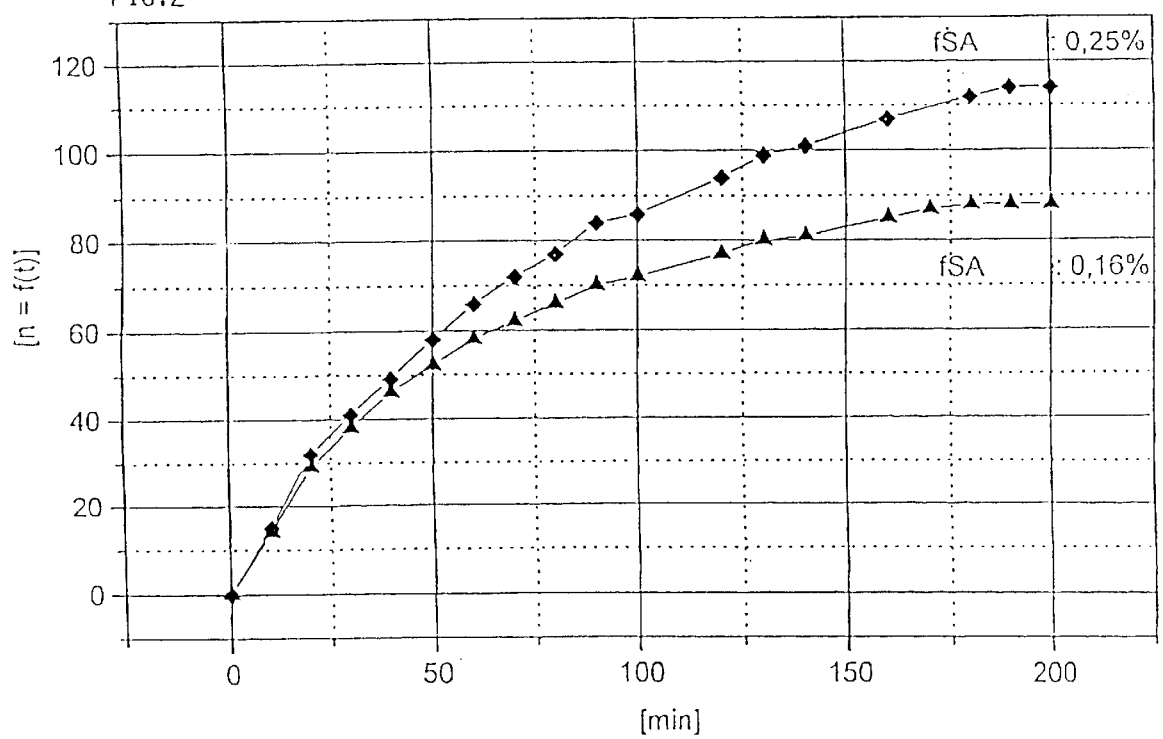
FIG. 2 shows the $CO_2$ evolution when the granulation vessel is a vacuum vessel.

Determination of the free salicylic acid gives 0.25% even with a dry citric acid not superficially passivated; the corresponding figure for a superficially passivated citric acid was 0.16%. As shown in FIG. 2, the $CO_2$ evolution was in both cases almost an order of magnitude lower than in Example 1.

Figure 3:
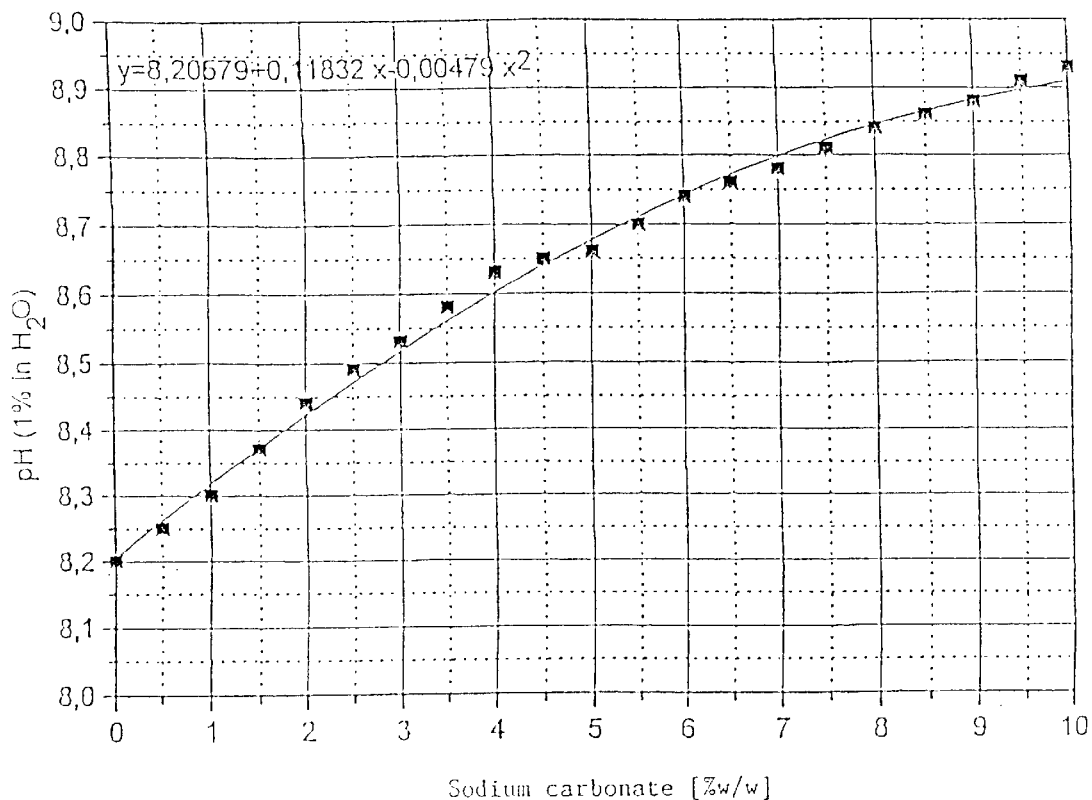
FIG. 3 shows the pH of a 1% solution when sodium bicarbonate is converted to sodium carbonate.

The conversion of sodium bicarbonate to sodium carbonate can be determined approximately and very simply by measuring the pH of a 1% solution (FIG. 3).

Instead of sodium bicarbonate, it is also possible, according to the invention, to treat potassium bicarbonate and achieve the same possible effect.

In both cases, the particle size does not play a serious role; fine powders to coarser crystals, for example of 0.3 mm, can successfully be treated if the conversion is continued to at least 1, preferably from 2 to 4, % by weight but not more than 10, preferably not more than 8, % by weight. Below 1%, the protective effect is dangerously low; above 10%, there may be problems with alkali-sensitive active ingredients, because sodium carbonate is alkaline. Because they have a larger surface area per unit weight, finer particle sizes are preferably reacted at the higher percentages within the stated range in order to achieve a uniform layer thickness.

The vacuum pump should have a nominal pumping capacity of at least 50, preferably at least 100, $m^3/h$.

EXAMPLE 3
(FIG. 4 to 8)

Figure 4:
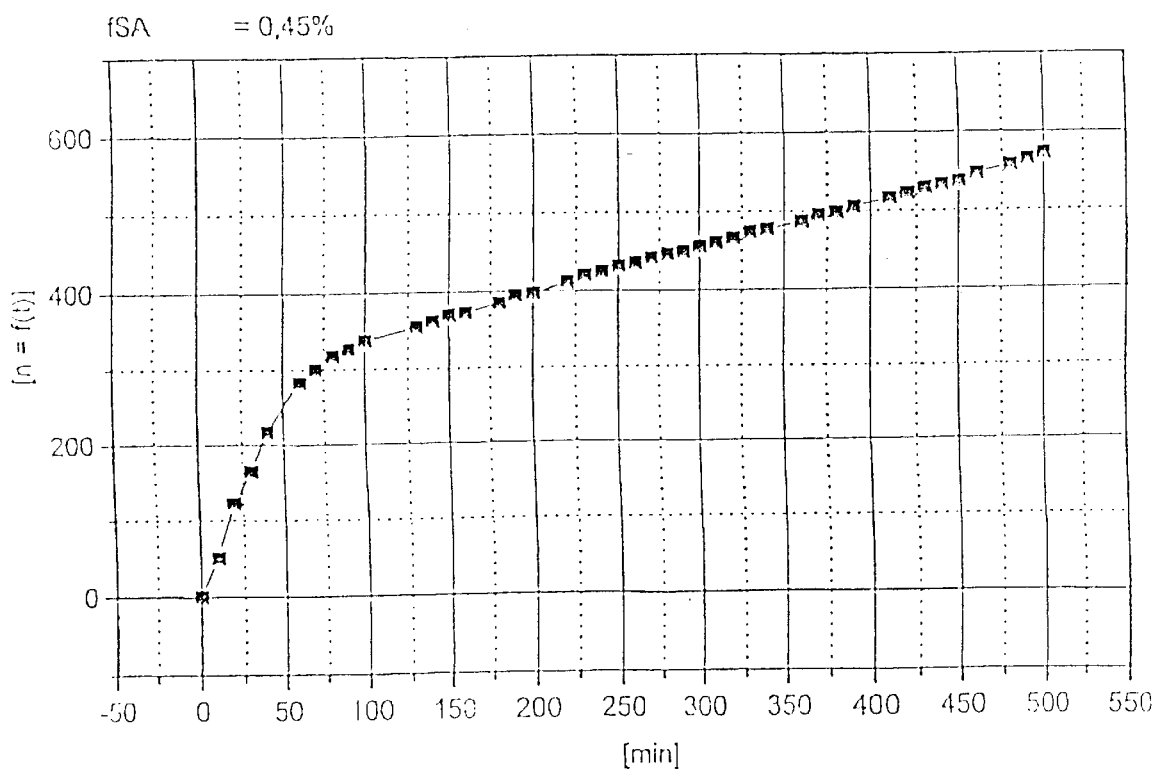
FIG. 4 shows the $CO_2$ evolution of an effervescent system with a fine-particled sodium bicarbonate having only 3.5% conversion.
Figure 5:
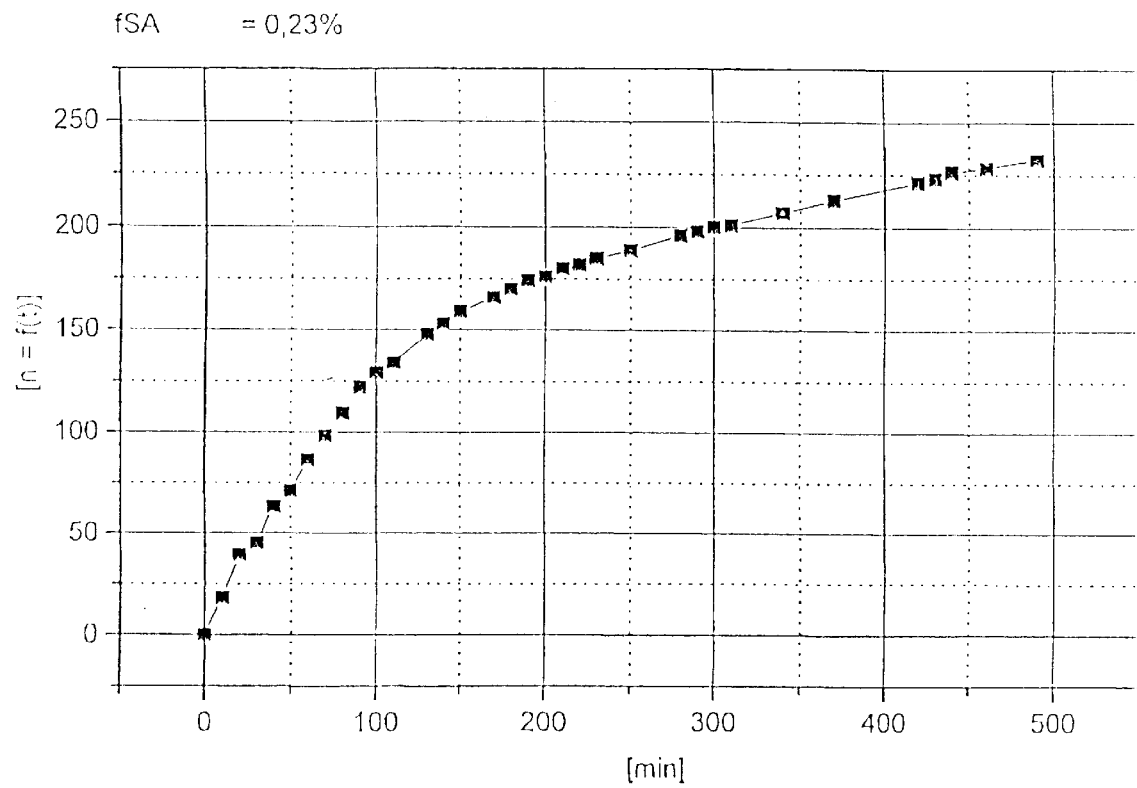
FIG. 5 shows the $CO_2$ evolution of an effervescent system with medium-coarse sodium bicarbonate having 3.4% conversion.
Figure 6:
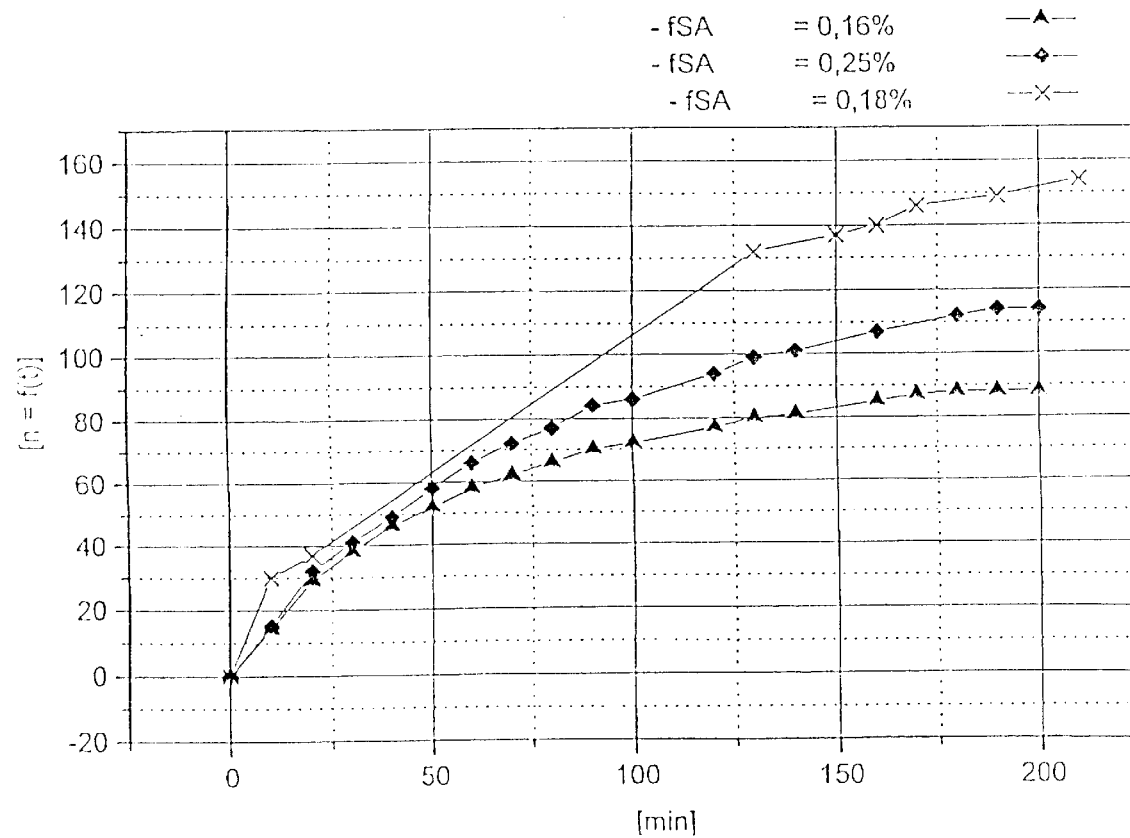
FIG. 6 shows the $CO_2$ evolution of an effervescent system with medium-coarse sodium bicarbonate having 8% conversion.
Figure 7:
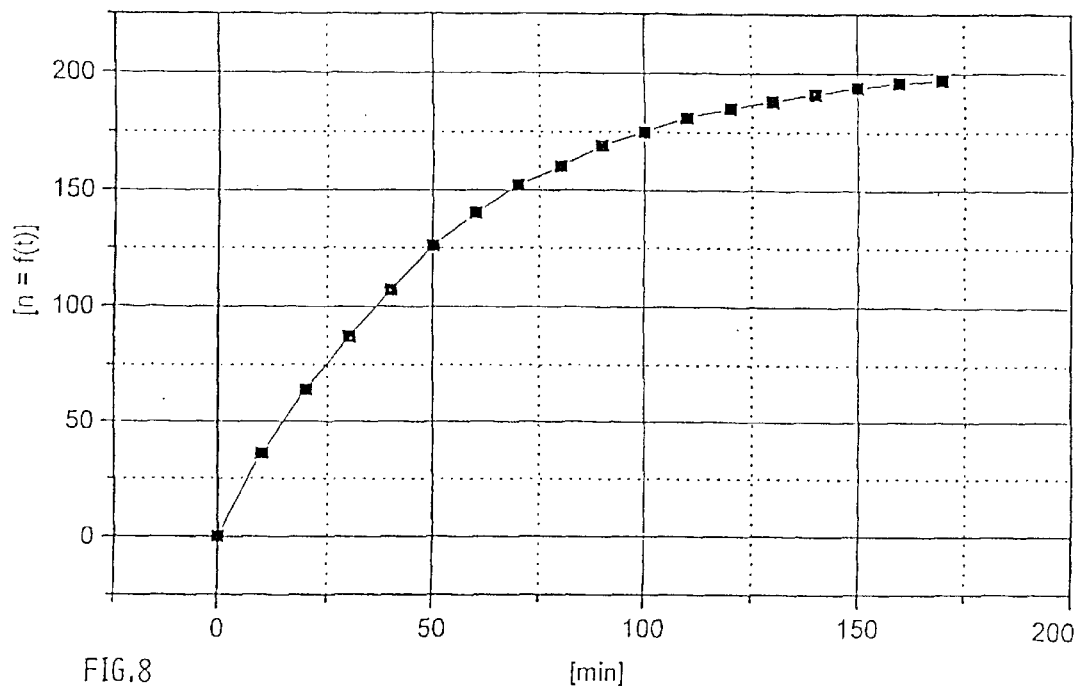
FIG. 7 shows the $CO_2$ evolution of an effervescent system with medium-coarse sodium bicarbonate having 9.5% conversion.
Figure 7:
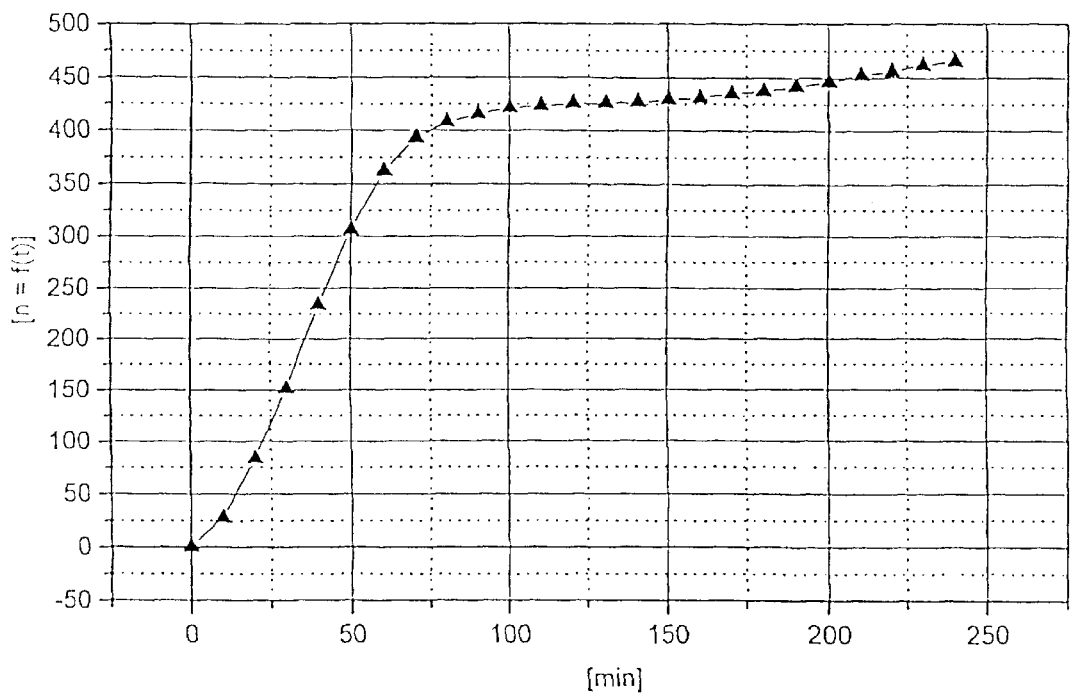

FIG. 4 to 7 show a few further curves (the time in minutes along the abscissa and the number of pulses along the ordinate) of the $CO_2$ evolution of effervescent systems according to the invention, prepared analogously to Example 2, in each case with data on the resulting free salicylic acid fSA, i.e. FIG. 4 with a fine-particled sodium bicarbonate having only 3.5% conversion and dried citric acid, FIG. 5 with medium-coarse sodium bicarbonate having 3.4% conversion and passivated citric acid. If the conversion is taken to 8% (FIG. 6, three parallel examples) or even to 9.5% (FIG. 7), both the $CO_2$ evolution and the formation of free salicylic acid are even further reduced.

In contrast, more than twice the amount of $CO_2$ is formed using a medium-coarse sodium bicarbonate converted to an extent of 6% without a vacuum (FIG. 8).

The invention is not restricted to the examples shown. As mentioned, it is also suitable, if necessary with suitable adaptation familiar to any relevant skilled worker, for further active ingredients which are sensitive to a component of the effervescent system or in particular to residual moisture.

We claim:

1. Effervescent system for effervescent tablets and/or effervescent granules, containing on the one hand particles of a solid, edible, organic acid and, on the other hand, particles of at least one alkali metal bicarbonate of which about 1 to about 4% by weight have been converted to alkali metal carbonate, wherein the alkali metal carbonate is an essentially cohesive layer on the alkali metal bicarbonate particles as well as essentially dry and free of water of crystallization.

2. Process for the preparation of alkali metal bicarbonate particles for an effervescent system according to claim 1, wherein commercial alkali metal bicarbonate particles are heat-treated in a vacuum vessel at less than 40 mbar at above 60° C. and are cooled to less than 60° C. after a time predetermined by the desired layer thickness, while maintaining the vacuum.

3. Process according to claim 2, wherein the vacuum is set to less than 20 mbar at between 80° and 120° C.

4. Process according to claim 3, wherein the vacuum is set to less than 10 mbar at about 100° C.

5. Process according to claim 2, wherein the vacuum vessel is cooled to less than 50° C.

6. Process according to claim 2, wherein the jacket of the vacuum vessel is preheated to a temperature of about 100° C. to about 120° C. before filling with the alkali metal bicarbonate particles.

7. Process according to claim 5, wherein the vacuum is established and maintained with the aid of a vacuum pump which has a nominal pumping capacity of at least 50 $m^3/h$, so that the vacuum never increases above 40 mbar during the treatment process.

8. Process according to claim 7, wherein the pumping capacity is at least 100 $m^3/h$ so that the vacuum never increases above 20 mbar.

* * * * *